(12) United States Patent
Wilhelm

(10) Patent No.: US 10,105,527 B2
(45) Date of Patent: Oct. 23, 2018

(54) BAYONET COUPLING ASSEMBLY

(71) Applicant: Colder Products Company, St. Paul, MN (US)

(72) Inventor: Grant Armin Wilhelm, Plymouth, MN (US)

(73) Assignee: Colder Products Company, St. Paul, MN (US)

( * ) Notice: Subject to any disclaimer, the term of this patent is extended or adjusted under 35 U.S.C. 154(b) by 492 days.

(21) Appl. No.: 14/812,085

(22) Filed: Jul. 29, 2015

(65) Prior Publication Data

US 2016/0033068 A1 Feb. 4, 2016

Related U.S. Application Data

(60) Provisional application No. 62/030,313, filed on Jul. 29, 2014.

(51) Int. Cl.
| | |
|---|---|
| *F16L 39/00* | (2006.01) |
| *A61M 39/10* | (2006.01) |
| *A61B 5/04* | (2006.01) |
| *A61B 5/022* | (2006.01) |
| *F16L 37/088* | (2006.01) |
| *F16L 37/098* | (2006.01) |
| *A61B 5/0402* | (2006.01) |

(Continued)

(52) U.S. Cl.
CPC .............. *A61M 39/10* (2013.01); *A61B 5/04* (2013.01); *A61B 5/022* (2013.01); *A61B 5/0402* (2013.01); *A61B 5/0476* (2013.01); *A61B 5/0488* (2013.01); *A61B 2562/225* (2013.01); *A61M 2039/1016* (2013.01); *A61M 2039/1027* (2013.01); *F16L 37/088* (2013.01); *F16L 37/0985* (2013.01)

(58) Field of Classification Search
CPC ... F16L 37/0841; F16L 37/088; F16L 37/091; F16L 37/0985
USPC ......................................... 285/308, 316, 317
See application file for complete search history.

(56) References Cited

U.S. PATENT DOCUMENTS

| | | | | |
|---|---|---|---|---|
| 1,096,690 A | * | 5/1914 | Derbyshire | ......... F16L 37/0841 |
| | | | | 285/277 |
| 4,471,978 A | * | 9/1984 | Kramer | ................... B60T 17/04 |
| | | | | 285/136.1 |

(Continued)

FOREIGN PATENT DOCUMENTS

| | | | | |
|---|---|---|---|---|
| DE | | 3634338 A1 * | 5/1987 | ............ F16L 37/086 |
| DE | | 9013145 U1 | 11/1990 | |

(Continued)

OTHER PUBLICATIONS

Lombardi, Frank, BPF220, Bayonet-Style Female Quick Connect Fitting, 200 Series Barb . . . , Value Plastics, Inc., copyright 2008, 1 page.

(Continued)

*Primary Examiner* — Aaron M Dunwoody
(74) *Attorney, Agent, or Firm* — Fish & Richardson P.C.

(57) ABSTRACT

A female coupling device includes: a main body defining a fluid passage therethrough; and a clip member coupled to the main body, with the clip member including two opposing arms that extend from the clip member at generally a 45 degree angle relative to a mating male coupling device, the arms being positioned to engage the male coupling device when the male coupling device is mated to the female coupling device.

19 Claims, 20 Drawing Sheets

(51) Int. Cl.
*A61B 5/0476* (2006.01)
*A61B 5/0488* (2006.01)

(56) References Cited

U.S. PATENT DOCUMENTS

| | | | |
|---|---|---|---|
| 4,969,879 A | 11/1990 | Lichte | |
| 6,062,537 A | 5/2000 | Chih | |
| 7,431,346 B2 * | 10/2008 | Frost | F16L 37/086 |
| | | | 285/307 |
| 2009/0194722 A1 * | 8/2009 | Tiberghien | F16L 37/0841 |
| | | | 251/149.6 |
| 2009/0261582 A1 * | 10/2009 | Gaudin | F16L 37/0841 |
| | | | 285/321 |
| 2011/0018258 A1 * | 1/2011 | Tiberghien | F16L 37/0847 |
| | | | 285/308 |
| 2011/0204622 A1 | 8/2011 | Lewis et al. | |
| 2011/0210541 A1 * | 9/2011 | Lewis | F16L 37/0841 |
| | | | 285/317 |
| 2013/0181437 A1 * | 7/2013 | Semmel | F16L 37/0847 |
| | | | 285/88 |
| 2013/0240048 A1 * | 9/2013 | Dankbaar | F16L 37/091 |
| | | | 137/15.01 |
| 2014/0197629 A1 * | 7/2014 | Barthel | F16L 37/0985 |
| | | | 285/93 |
| 2017/0045169 A1 * | 2/2017 | Gibelin | F16L 37/0841 |
| 2017/0045170 A1 * | 2/2017 | Lewis | A61B 5/02233 |
| 2017/0284581 A1 * | 10/2017 | Ackermann | F16L 37/0841 |

FOREIGN PATENT DOCUMENTS

| | | | |
|---|---|---|---|
| DE | 4300037 C1 | 4/1994 | |
| GB | 2036906 A * | 7/1980 | F16L 37/086 |
| JP | 06117586 A * | 4/1994 | |
| WO | 2006036192 A1 | 4/2006 | |
| WO | 2006039501 A2 | 4/2006 | |

OTHER PUBLICATIONS

International Search Report and Written Opinion in PCT/US2015/042632 dated Oct. 21, 2015, 14 pages.

* cited by examiner

BAYONET COUPLING ASSEMBLY

CROSS-REFERENCE TO RELATED APPLICATIONS

This application claims priority to U.S. application Ser. No. 62/030,313, filed on Jul. 29, 2014.

BACKGROUND

Coupling assemblies typically include female and male couplings that are connected to create a fluid flow path therebetween. Such coupling assemblies can be used in various applications, including biomedical applications.

For example, the coupling assemblies can be used in such applications as to couple a blood pressure cuff to a sphygmomanometer machine. In such a configuration, the coupling assembly can be referred to as a bayonet connector. This is a 'push-to-connect' type coupling, meaning that the male coupling device can be coupled to the female coupling device simply by pushing the two together (some couplings require an additional step or two).

SUMMARY

In one aspect, a female coupling device includes: a main body defining a fluid passage therethrough; and a clip member coupled to the main body, with the clip member including two opposing arms that extend from the clip member at generally a 45 degree angle relative to a mating male coupling device, the arms being positioned to engage the male coupling device when the male coupling device is mated to the female coupling device.

DESCRIPTION OF THE DRAWINGS

Reference is now made to the accompanying drawings, which are not necessarily drawn to scale.

DETAILED DESCRIPTION

Figure 1:
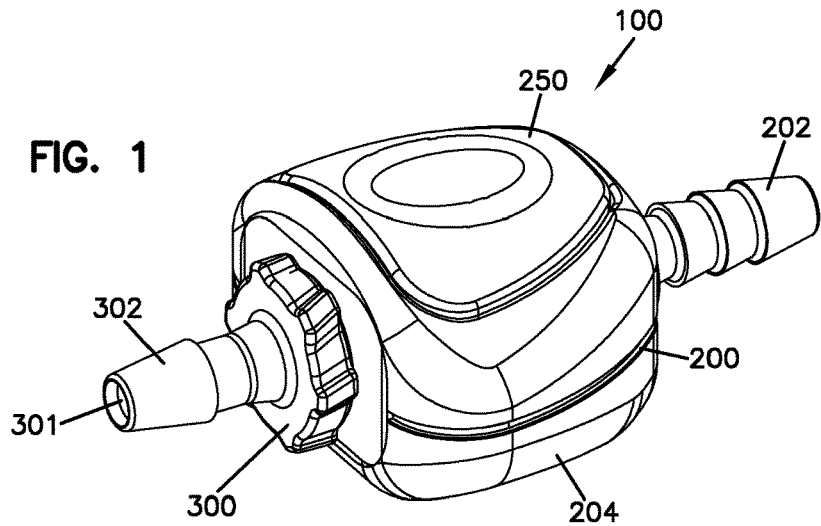
FIG. 1 is a perspective view of an example coupling assembly.
Figure 2:
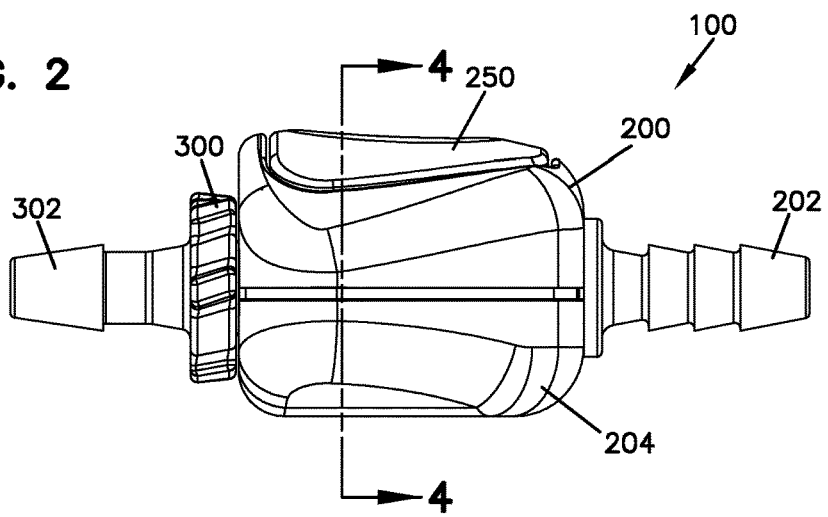
FIG. 2 is a side view of the coupling assembly of FIG. 1.
Figure 3:
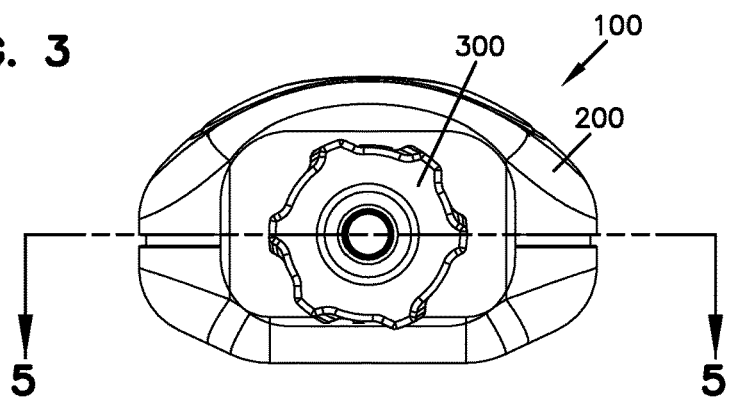
FIG. 3 is an end view of the coupling assembly of FIG. 1.
Figure 4:
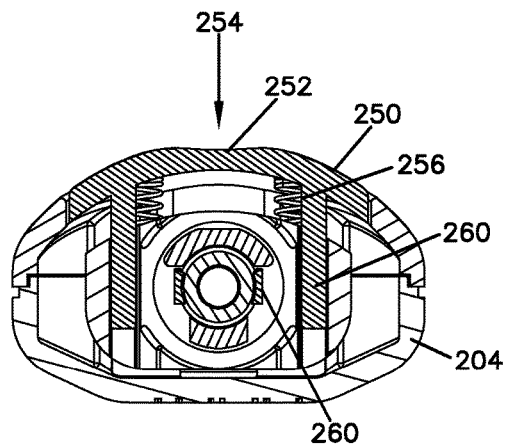
FIG. 4 is a cross-sectional view along line 4-4 of the coupling assembly of FIG. 2.
Figure 5:
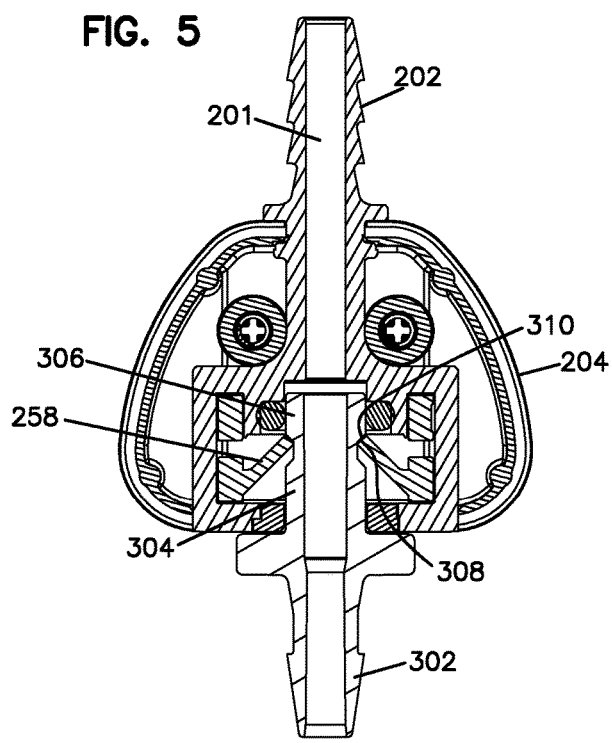
FIG. 5 is a cross-sectional view along line 5-5 of the coupling assembly of FIG. 3.
Figure 6:
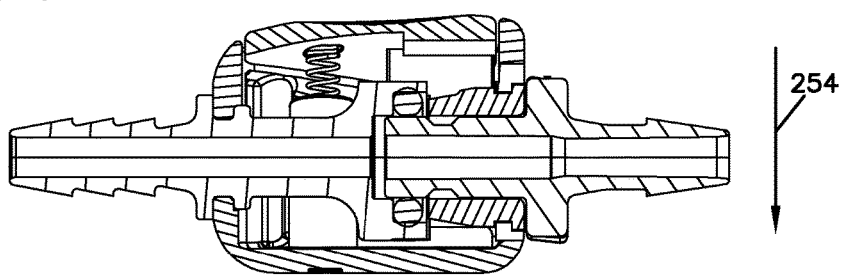
FIG. 6 is a cross-sectional view of the coupling assembly of FIG. 1.
Figure 7:
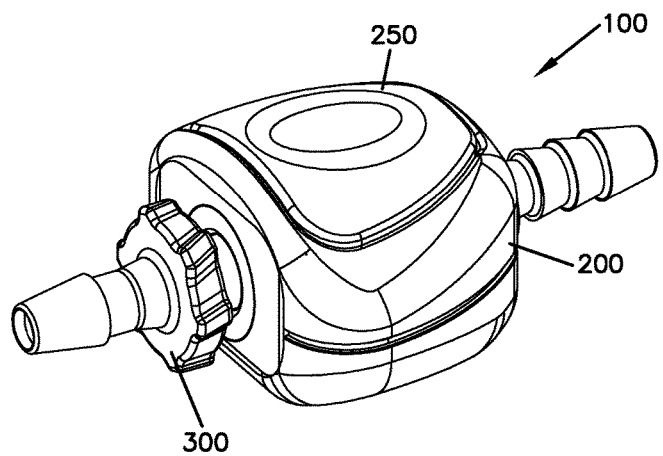
FIG. 7 is a perspective view of the coupling assembly of FIG. 1 with an example male coupling device being partially inserted into an example female coupling.
Figure 8:
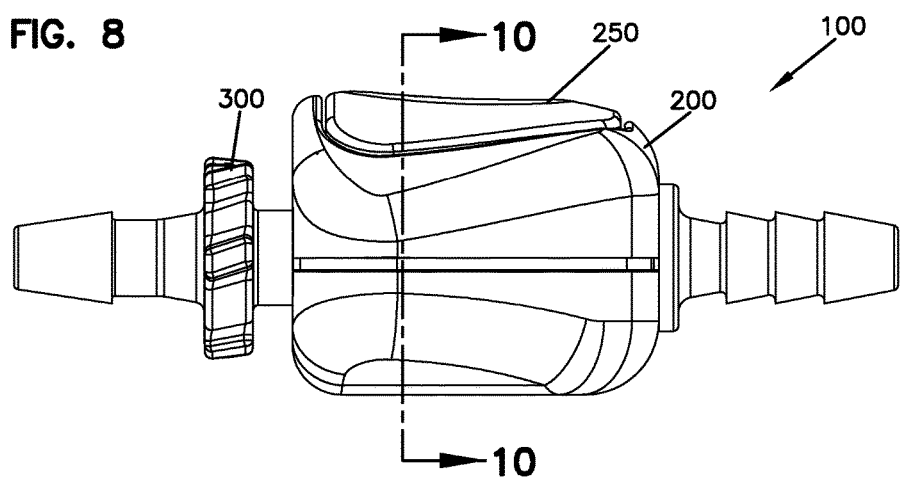
FIG. 8 is a side view of the coupling assembly of FIG. 7.
Figure 9:
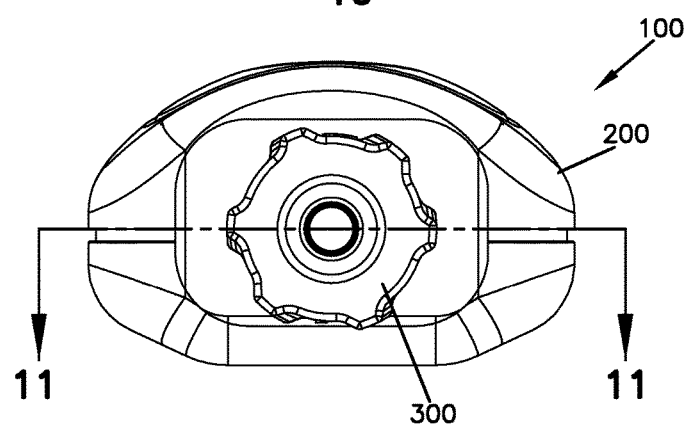
FIG. 9 is an end view of the coupling assembly of FIG. 7.
Figure 10:
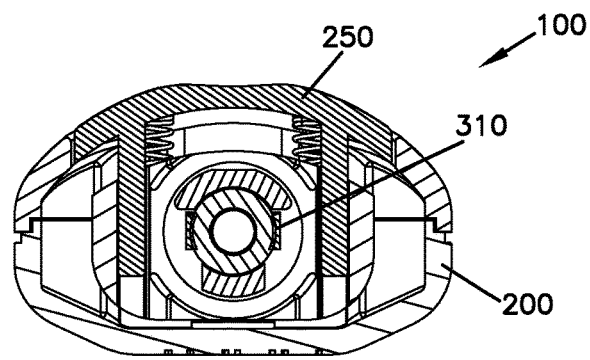
FIG. 10 is a cross-sectional view along line 10-10 of the coupling assembly of FIG. 8.
Figure 11:
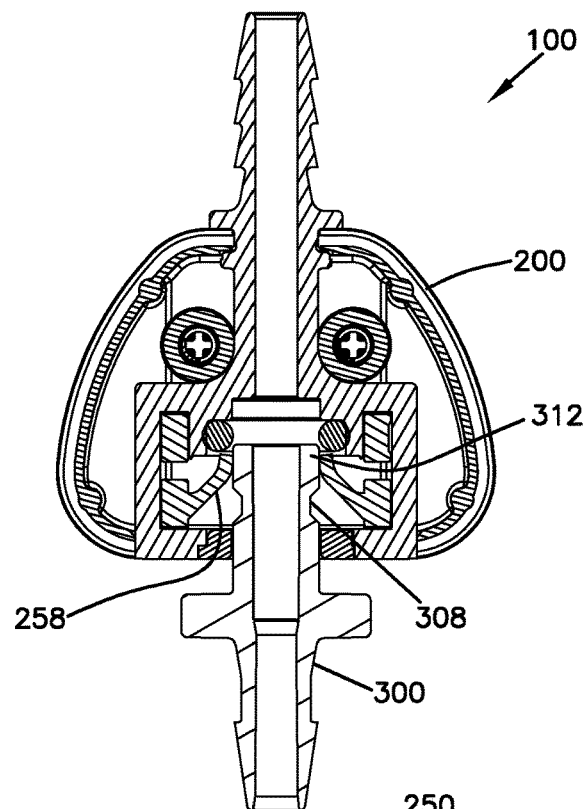
FIG. 11 is a cross-sectional view along line 11-11 of the coupling assembly of FIG. 9.
Figure 12:
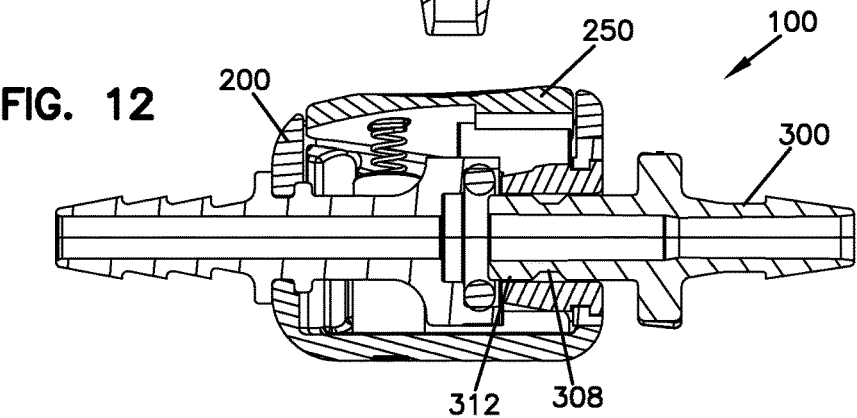
FIG. 12 is a cross-sectional view of the coupling assembly of FIG. 7.
Figure 13:
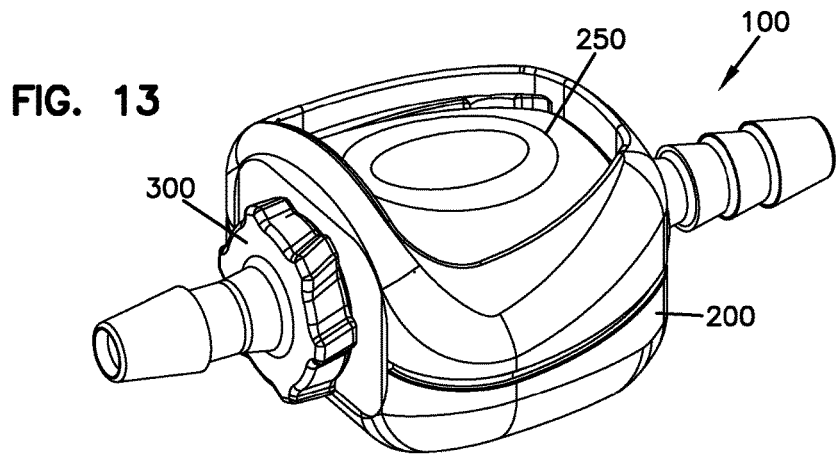
FIG. 13 is a perspective view of the coupling assembly of FIG. 1 with the clip member depressed.
Figure 14:
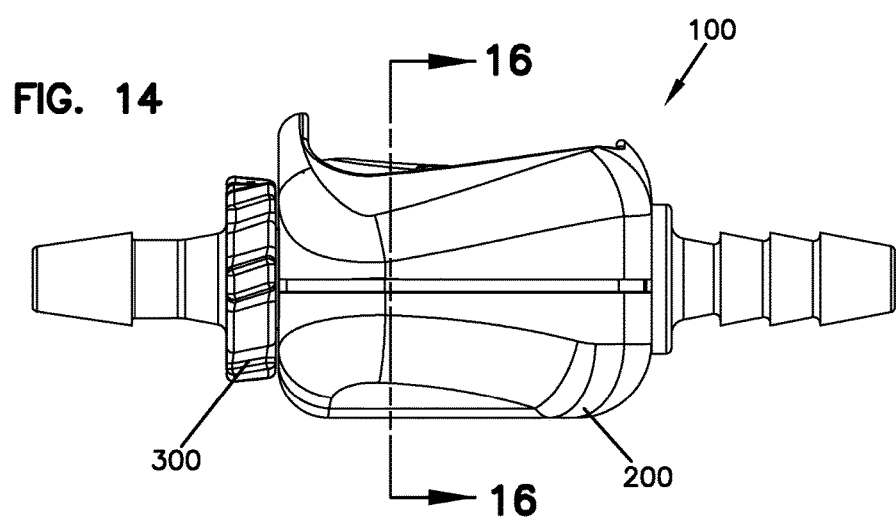
FIG. 14 is a side view of the coupling assembly of FIG. 13.
Figure 15:
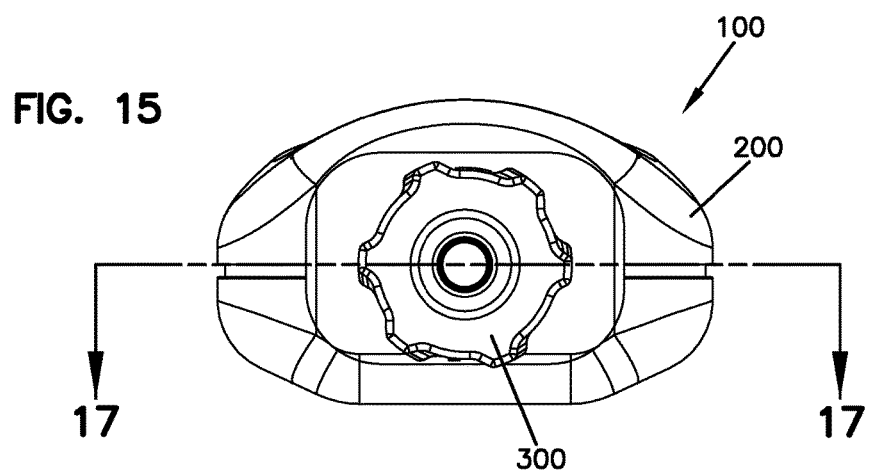
FIG. 15 is an end view of the coupling assembly of FIG. 13.
Figure 16:
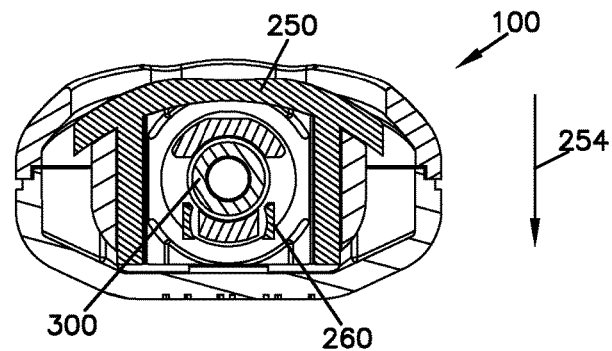
FIG. 16 is a cross-sectional view along line 16-16 of the coupling assembly of FIG. 14.

The present disclosure relates to a bayonet coupling assembly. In some examples, the bayonet coupling assembly is used in conjunction with a biomedical device, such as a sphygmomanometer. Other configurations are possible.

In the examples described herein, the coupling assembly is non-valved. However, in other examples, the coupling assembly can be valved. In the embodiment shown, the female coupling device includes "retainers" that hold the male coupling device in the coupled position. The retainers are a pair of cantilever arms that are integrally molded with a clip member, although separate arms are possible. The retainers are positioned at a 45 degree angle with respect to the male coupling device, which is perpendicular to the contact surface.

In this example configuration, the cantilevers can be loaded axially (a stable orientation) when coupled. During the connection process, the cantilevers can deform outward and allow the male coupling device to pass into the female coupling device and into the coupled position. To disconnect the male coupling device, the clip member is depressed and the cantilevers move to a clearance position and allow the male coupling device to be removed.

Referring now to FIGS. 1-6, an example coupling assembly 100 is shown. The coupling assembly includes a female coupling device 200 and a male coupling device 300.

The female coupling device 200 includes a main body 204 and a termination 202. See FIGS. 1-6 and 19-23. The main body 204 forms a fluid passageway 201 therethrough. In these examples, fluid can be any type of fluid, such as a liquid or gas (e.g., air). The female coupling device 200 can be formed using known techniques, such as sonic welding, staking, press-fitting, and threading.

Figure 28:
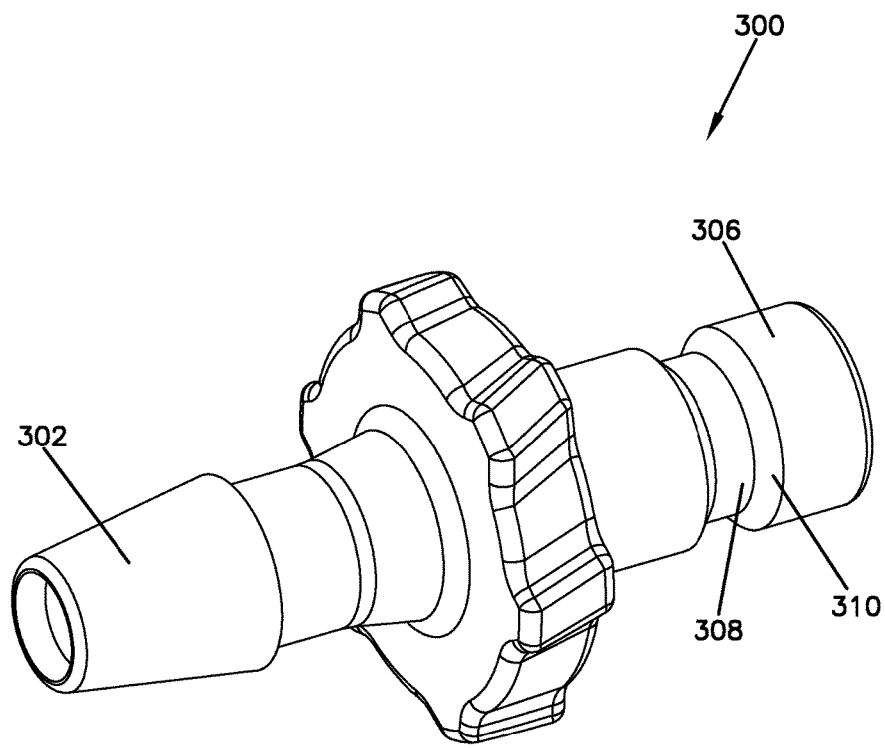
FIG. 28 is a perspective view of an example male coupling device of the coupling assembly of FIG. 1.
Figure 29:
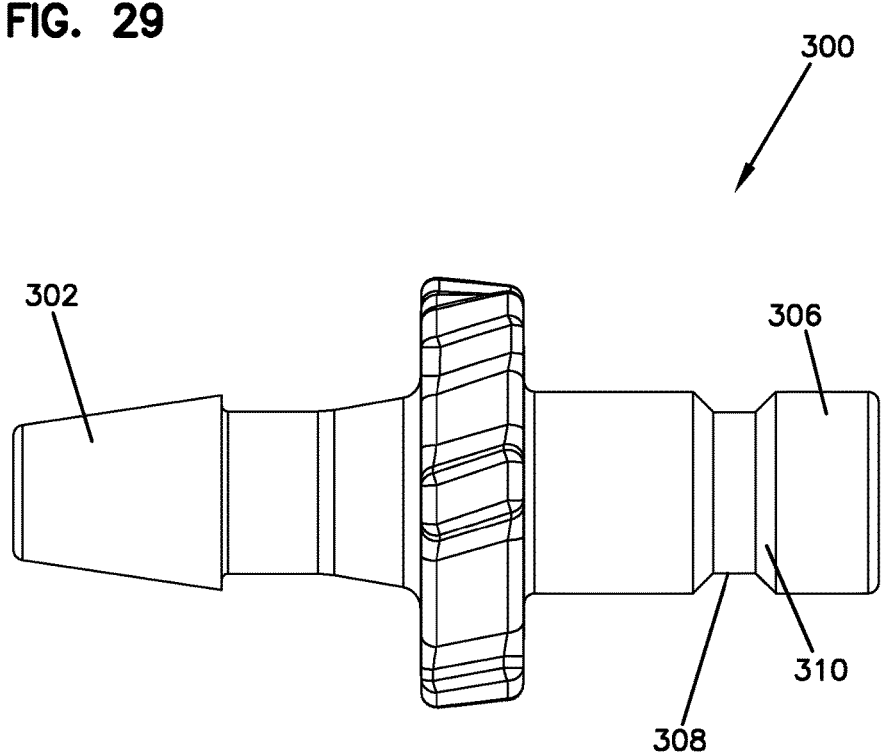
FIG. 29 is a side view of the male coupling device of FIG. 28.
Figure 30:
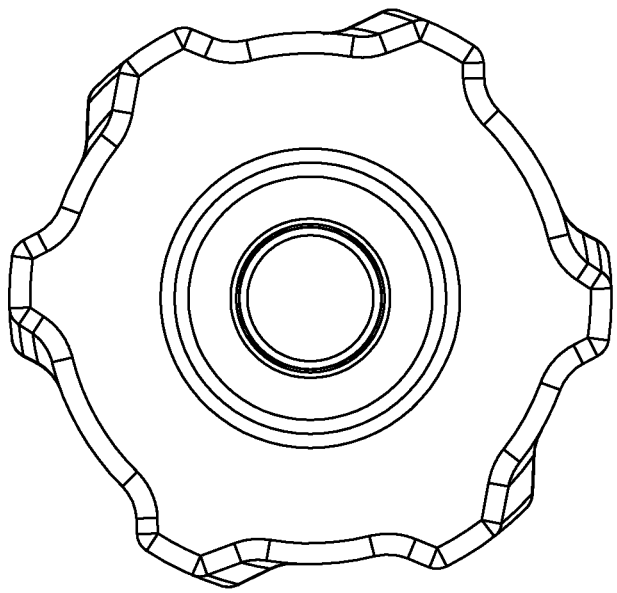
FIG. 30 is an end view of the male coupling device of FIG. 28.
Figure 31:
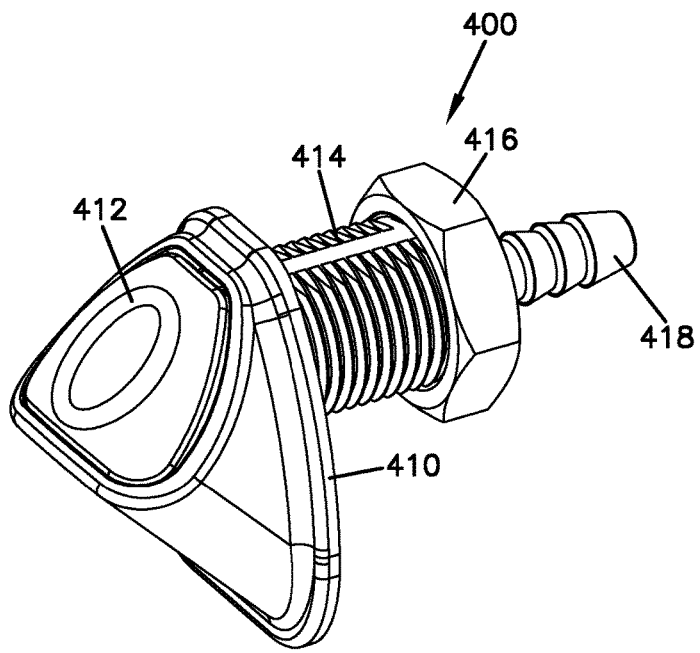
FIG. 31 is a perspective view of another example female coupling device.
Figure 32:
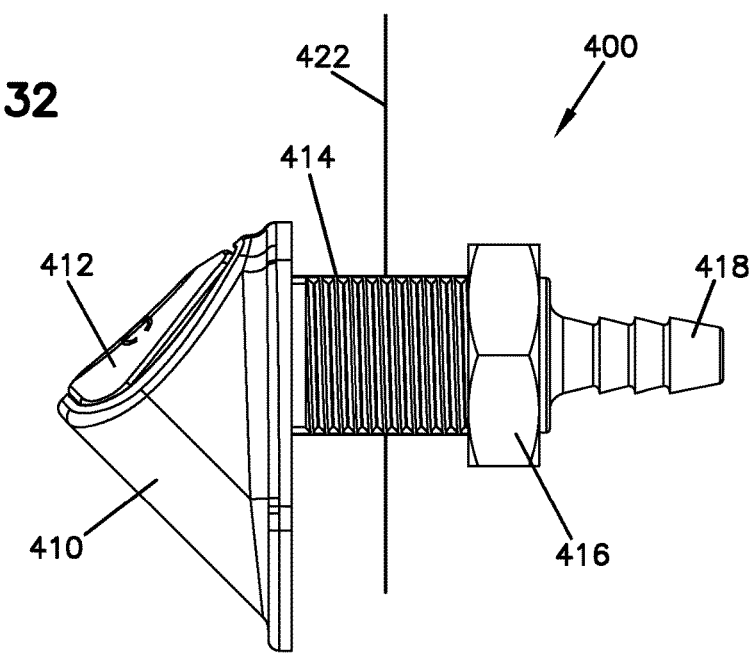
FIG. 32 is a side view of the female coupling device of FIG. 31.
Figure 33:
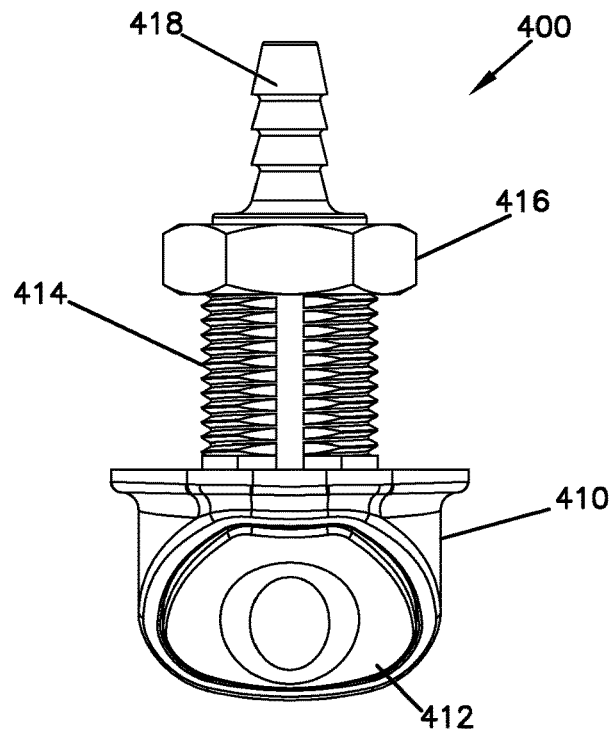
FIG. 33 is a top view of the female coupling device of FIG. 31.
Figure 34:
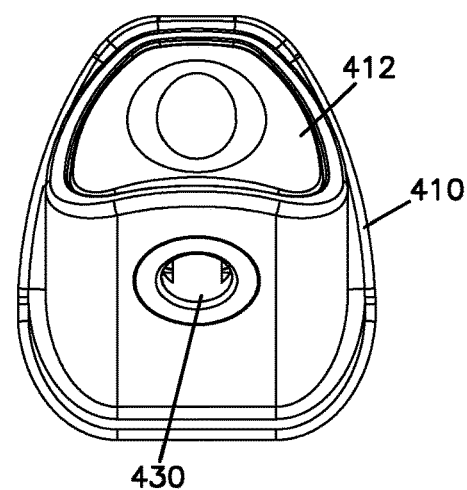
FIG. 34 is a front view of the female coupling device of FIG. 31.

The male coupling device 300 includes a main body 304 and a termination 302. The main body 304 forms a fluid passageway 301 therethrough. See FIGS. 28-30.

The terminations 202, 302 are configured to be coupled to another component, such as fluid lines and/or devices. For example, in one embodiment, the termination 302 is connected to a fluid line extending to a blood pressure cuff. The termination 202 is connected to a fluid line extending to a pump unit of a sphygmomanometer. Fluid (i.e., air) is provided from the pump until to the blood pressure cuff through the coupling assembly 100 when the female coupling device is coupled to the male coupling device 300, as described further below.

Other configurations are possible. For example, the female coupling device 200 can be formed independently, as shown, or can be incorporated into the pump unit of the sphygmomanometer. In other examples, the coupling assembly 100 can be used in other applications, both biomedical and elsewhere. For example, the coupling assembly can be used for "shop air" applications, sometimes referred to as "industrial interchange connectors." In these examples, pressurized air is delivered through the coupling assembly, so the coupling assembly can be modified, such as by using clip cantilevers having pivoting arms.

The female coupling device 200 includes a clip member 250. The clip member 250 moves in a direction 254 (see FIGS. 4 and 6) between locked and unlocked positions. This will be described further below.

As shown in FIGS. 1-6, the clip member 250 is in the locked position. Springs 256 force the clip member 250 into this locked position. As shown best in FIGS. 24-27, the clip member 250 forms retainers that include cantilever arms 258 that extend from the clip member 250. When in the locked position, the arms 258 engage a clip groove 308 formed in a body 304 of the male coupling device 300 to retain the male coupling device 300 in the female coupling device 200. See FIGS. 28-30.

Specifically, an end 260 of each of the arms 258 is contoured to follow the general shape of the mating male coupling device 300. When in this position (see FIG. 5), the arms 258 extend at a 45 degree angle relative to the male coupling device 300. Other angles can be used, such as angles between 30 and 70 degrees. In yet other examples, the arms 258 can be perpendicular to the mating surface of the male coupling device 300. In such examples, the shape of the clip groove 308 can be modified, such as a non-square clip groove can be used.

The ends 260 engage a wall 310 formed in the clip groove 308. The arms 258 thereby resist movement of the male coupling device 300 out of the female coupling device 200.

Figure 17:
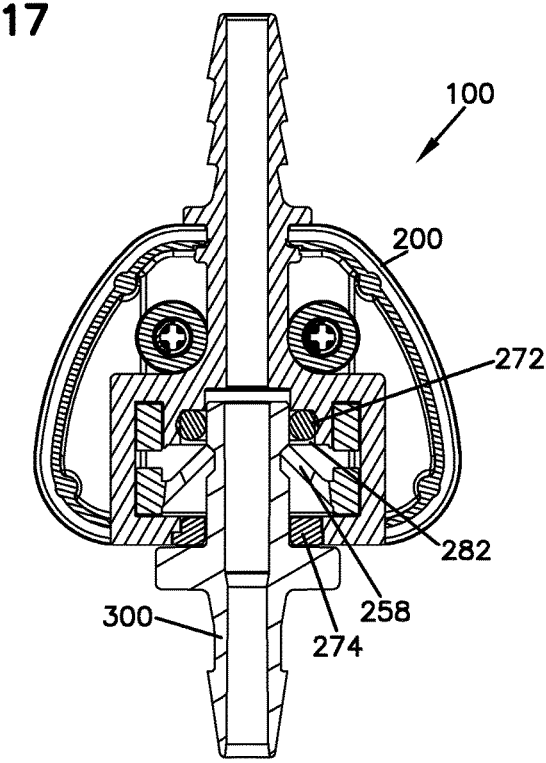
FIG. 17 is a cross-sectional view along line 17-17 of the coupling assembly of FIG. 15.
Figure 18:
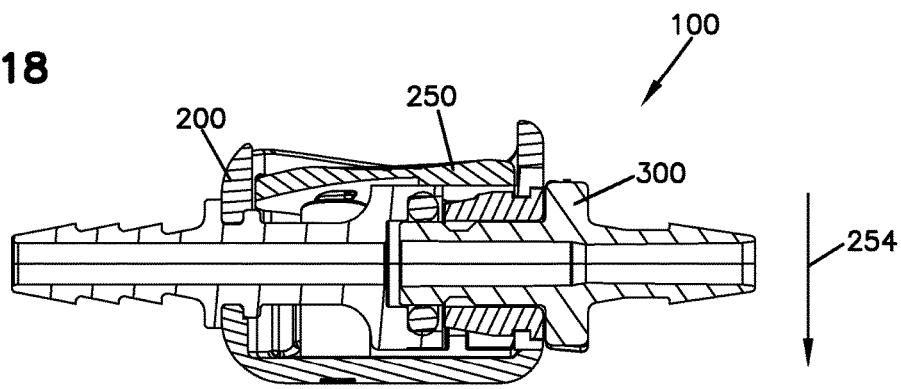
FIG. 18 is a cross-sectional view of the coupling assembly of FIG. 13.
Figure 19:
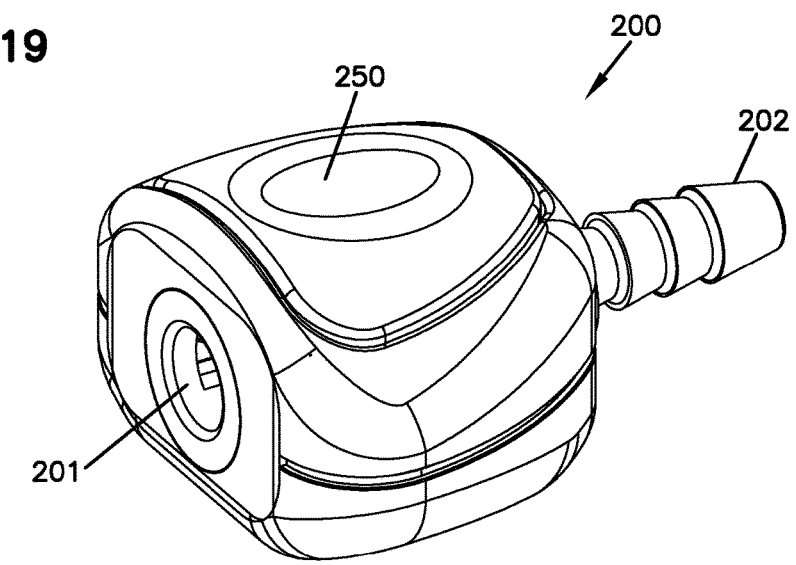
FIG. 19 is a perspective view of an example female coupling device of the coupling assembly of FIG. 1.
Figure 20:
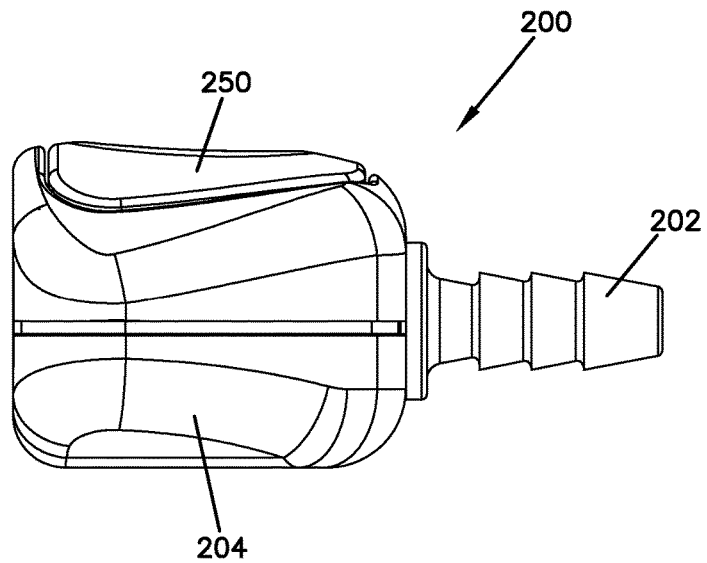
FIG. 20 is a side view of the female coupling device of FIG. 19.
Figure 21:
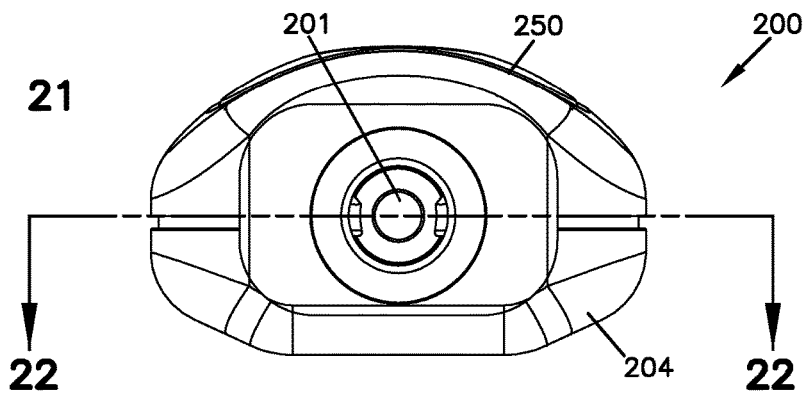
FIG. 21 is an end view of the female coupling device of FIG. 19.
Figure 22:
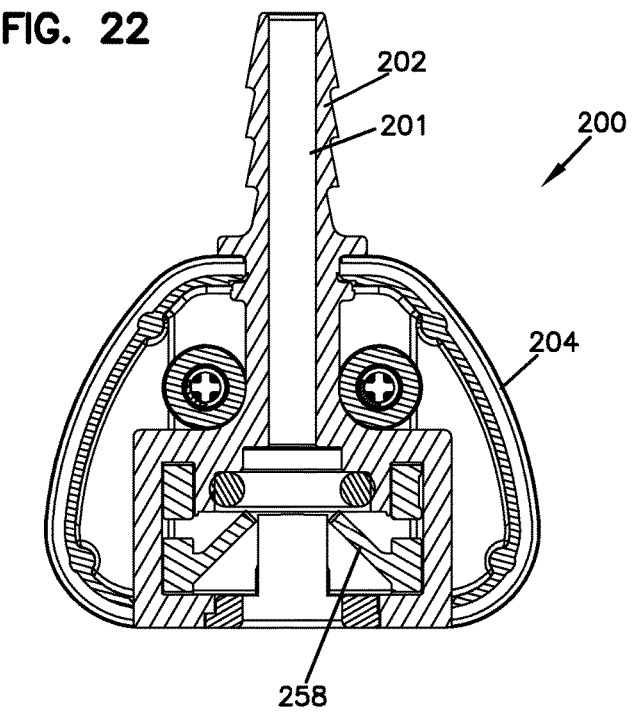
FIG. 22 is a cross-sectional view of the female coupling device of FIG. 19.
Figure 23:
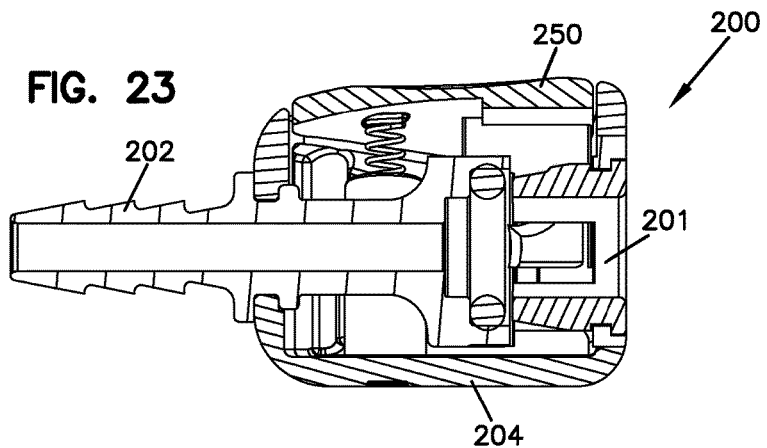
FIG. 23 is another cross-sectional view of the female coupling device of FIG. 19.
Figure 24:
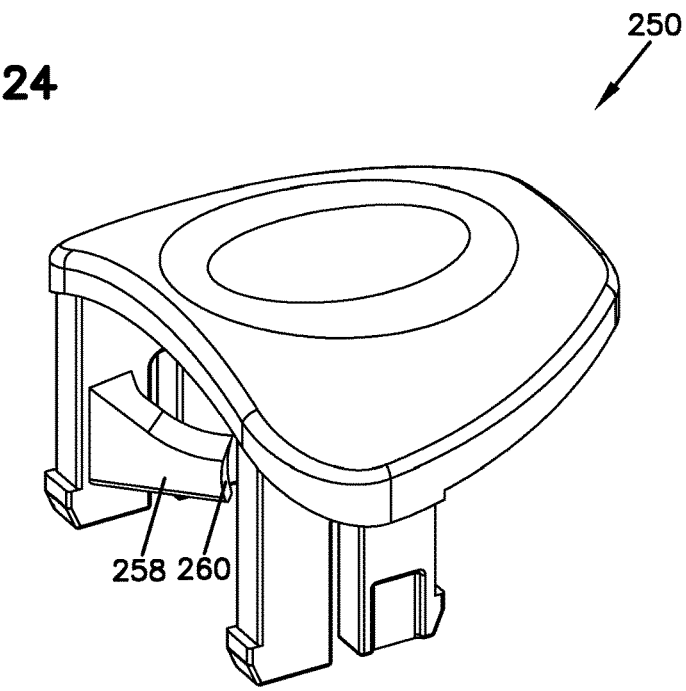
FIG. 24 is a perspective view of an example clip member of the female coupling device of FIG. 19.
Figure 25:
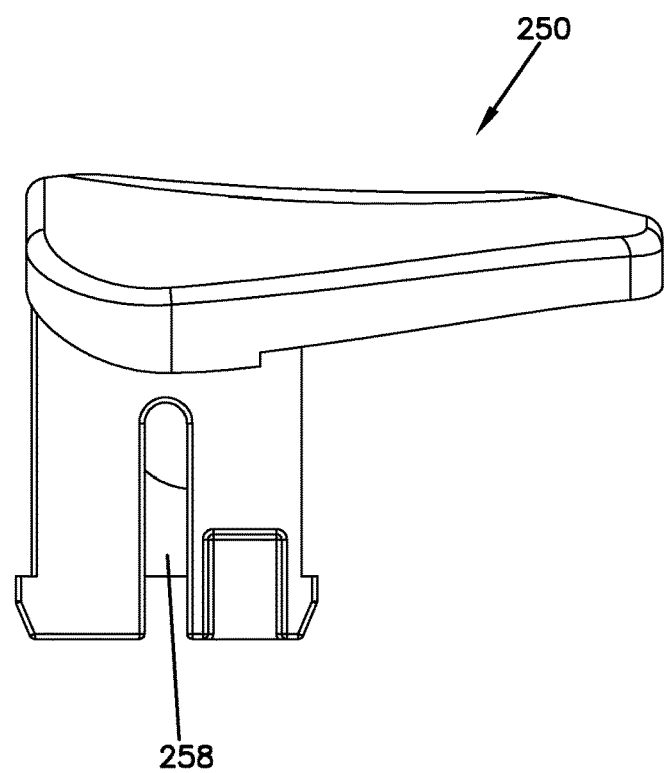
FIG. 25 is a side view of the clip member of FIG. 24.
Figure 26:
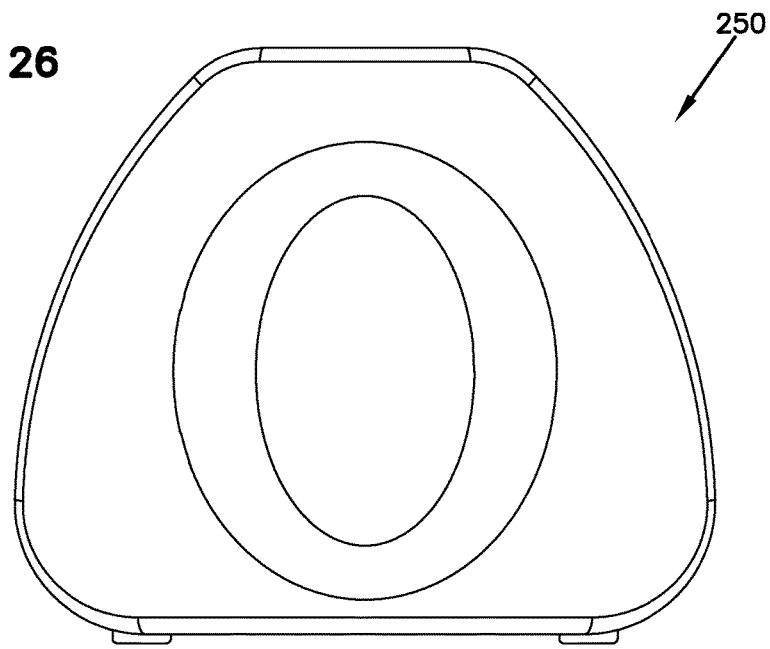
FIG. 26 is a top view of the clip member of FIG. 24.
Figure 27:
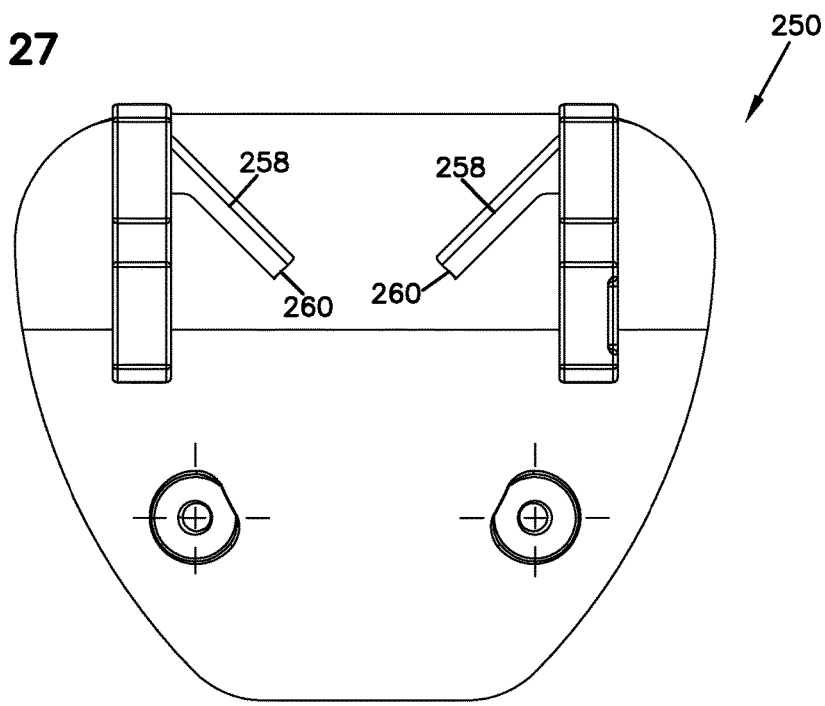
FIG. 27 is a bottom view of the clip member of FIG. 24.

The female coupling assembly 200 also includes a seal 272 configured to seal against the mating male coupling device 300. The seal 272 is an O-ring in this embodiment, although other sealing arrangements can be used. In this example, the seal 272 (see FIG. 17) is a captured seal, in that the groove in which the seal 272 is placed is formed in part by a portion 282 of the clip member 250. This allows the seal 272 to be positioned closers to the male coupling device 300. In addition, the seal 272 is held by a retaining member 274, which is described further below with reference to FIGS. 36-43.

Referring now to FIGS. 7-12, to coupling the male coupling device 300 to the female coupling device 200, the male coupling device 300 is inserted into the fluid passageway 201 of the female coupling device. During insertion, the arms 258 deform outward (i.e., flex or move out of the way) and ride along a surface 312 of the male coupling device 300 (see FIG. 11) to allow the male coupling device 300 to pass into the female coupling device 200 and into the coupled position. Once in the fully-inserted position, the arms 258 engage the wall 310 of the clip groove 308 to retain the male coupling device 300 in the female coupling device 200, as shown in FIGS. 1-6.

Referring now to FIGS. 13-18, to disconnect the male coupling device 300 from the female coupling device, the clip member 250 is depressed in the direction 254. In this unlocked position, the arms 258 move to a clearance position where the arms are located outside (i.e., below) the clip groove 308. This allows the arms 258 to clear the clip groove 308, and the male coupling device 300 can thereupon be removed from the female coupling device 200.

Once the clip member 250 is released, the springs 256 move the clip member 250 back to the upper locked position. The clip member 250 is thereupon ready for reinsertion of the male coupling device 300, as shown in FIGS. 6-12.

Referring now to FIGS. 31-35, another example female coupling device 400 is shown. The female coupling device 400 is similar in configuration to that of the female coupling device 200 described above, with noted exceptions below. The female coupling device 400 is configured to mate with a male coupling device, such as the male coupling device 300 described above.

The female coupling device 400 includes a body 410 and a clip member 412 configured in a manner identical to that of the clip member 250 described above. The female coupling device 400 also includes a termination 418 configured to be connected to a fluid line or other destination for fluid flowing through the female coupling device 400.

The female coupling device 400 also includes a threaded portion 414 and a nut 416 positioned thereon. The threaded portion 414 is sized to be received through an opening formed in a panel, such as a panel 422 depicted in FIG. 32. In this configuration, the female coupling device 400 is attached to a panel of an apparatus or other device by positioning the threaded portion 414 through the panel opening and threading the nut 416 onto the threaded portion 414 until the panel 422 is captured between the nut 416 and the body 410, thereby affixing the female coupling device 400 to the panel 422.

Figure 35:
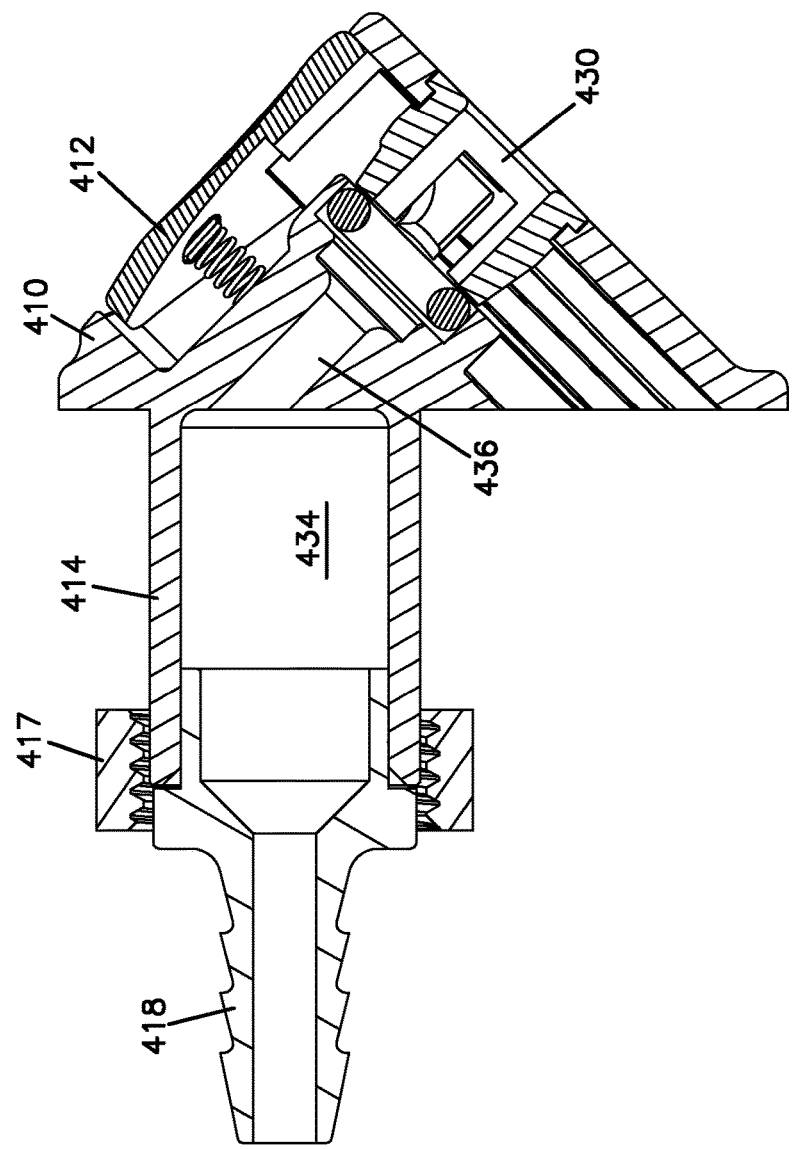
FIG. 35 is a cross-sectional view of the female coupling device of FIG. 31.
Figure 36:
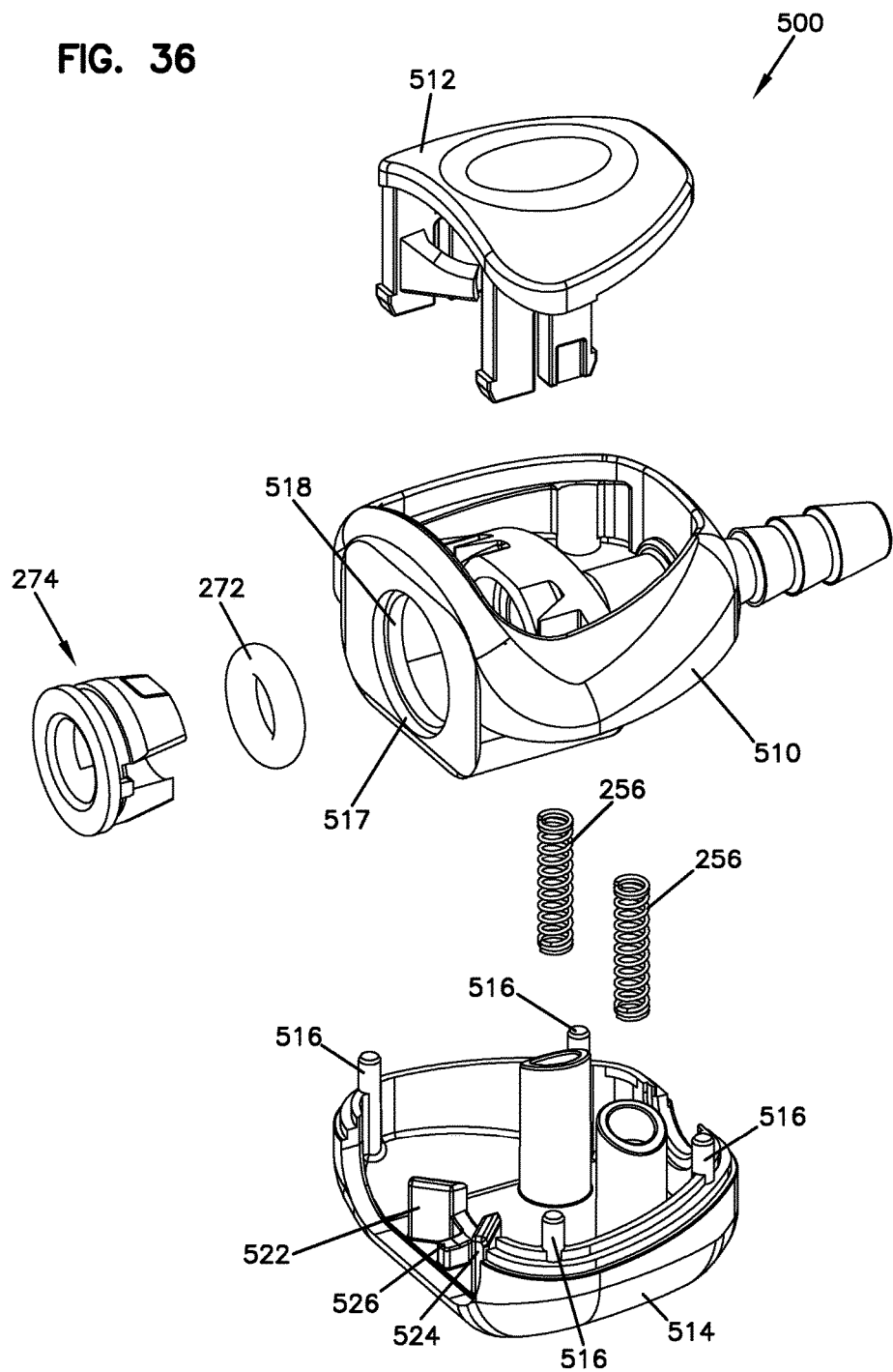
FIG. 36 is an exploded view of another example female coupling device.
Figure 37:
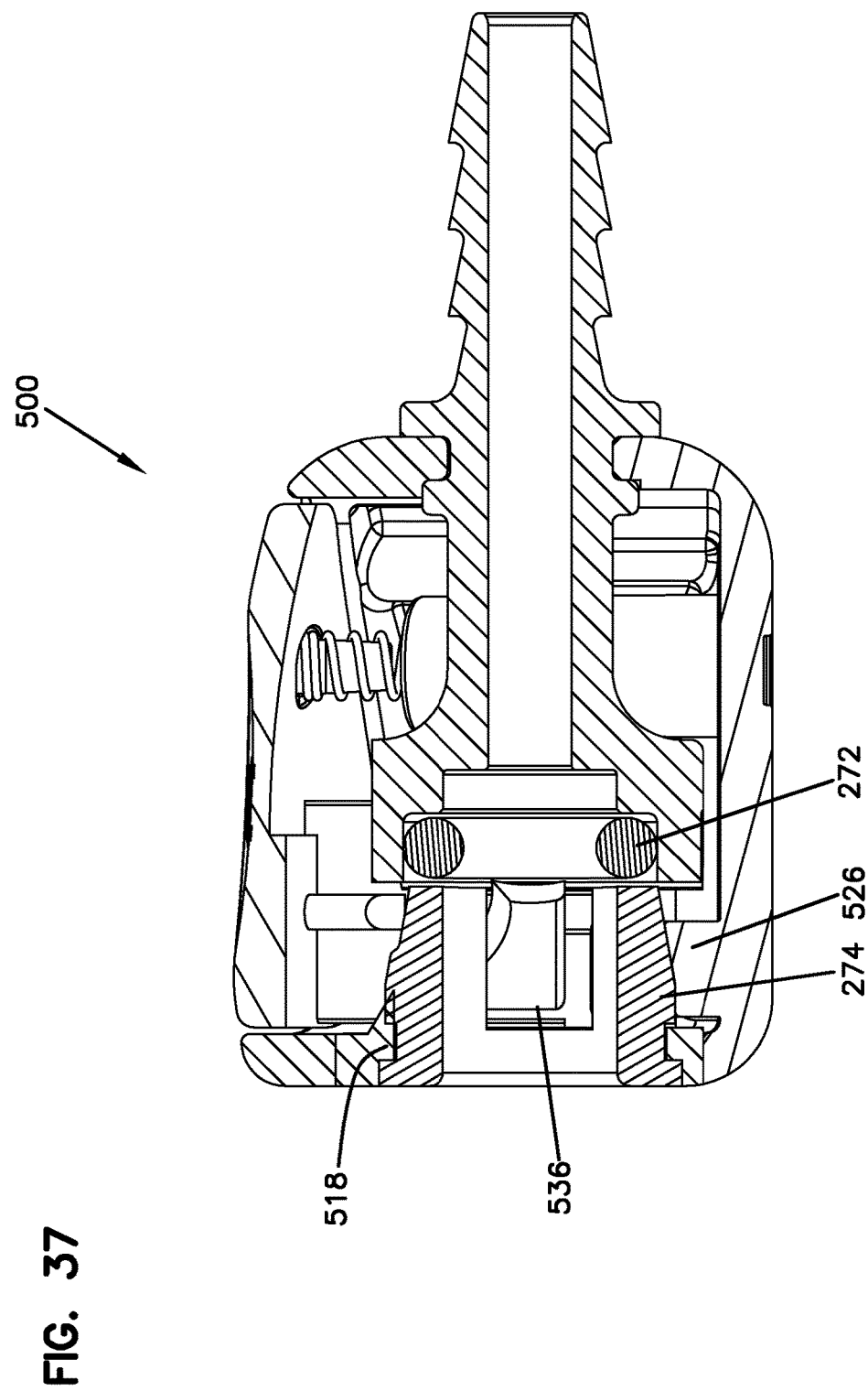
FIG. 37 is a cross-sectional view of the female coupling device of FIG. 36.
Figure 38:
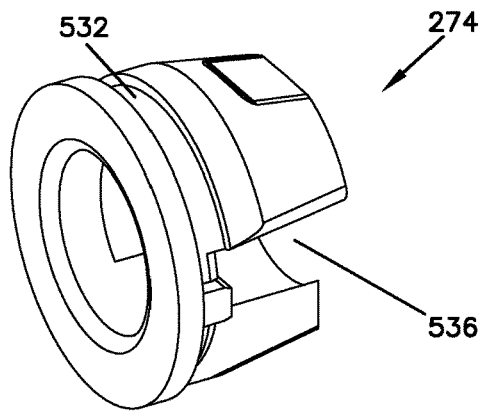
FIG. 38 is a perspective view of an example retaining member of the female coupling device of FIG. 36.
Figure 39:
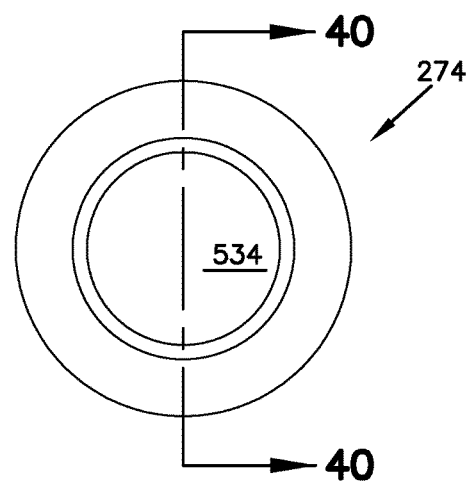
FIG. 39 is a front view of the retaining member of FIG. 38.
Figure 40:
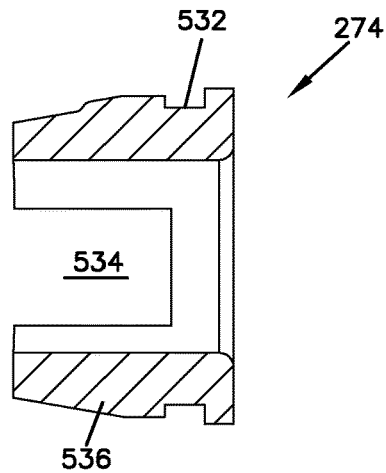
FIG. 40 is a cross-sectional view of the retaining member of FIG. 39.
Figure 41:
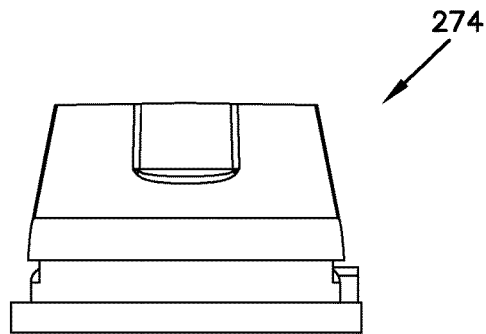
FIG. 41 is a top view of the retaining member of FIG. 38.
Figure 42:
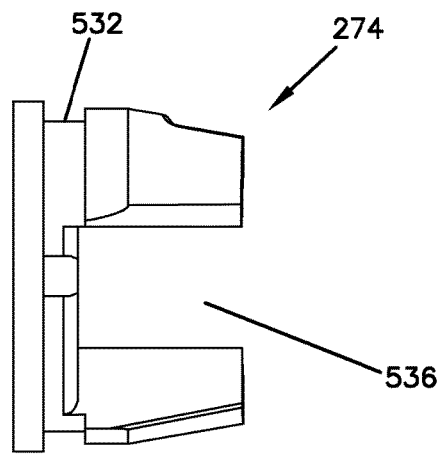
FIG. 42 is a side view of the retaining member of FIG. 38.
Figure 43:
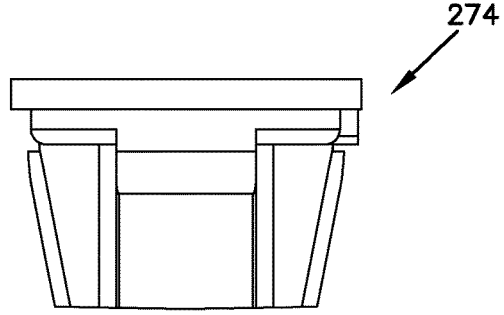
FIG. 43 is a bottom view of the retaining member of FIG. 38.

As shown in FIG. 35, the female coupling device 400 forms an opening 430 in the body 410 through which mating male coupling device is positioned. The body 410 forms a passageway 432 in communication with the opening 430 that extends to a passageway 434 formed through the threaded portion 414. In this example, the passageway 432 is positioned at an angle relative to the passageway 434. In one example, the angle formed between the passageways 432, 434 is approximately 30 or 45 degrees. Other configuration, such as a straight passage, can also be used.

Referring now to FIGS. 36-43, another example female coupling device 500 is shown. The female coupling device 500 is similar in configuration to that of the female coupling device 200 described above, with noted exceptions below. The female coupling device 500 is configured to mate with a male coupling device, such as the male coupling device 300 described above.

The female coupling device 500 includes a body 510 and a clip member 512 configured in a manner similar to that of the clip member 250 described above. The coupling device 500 also includes a bottom portion 514 that is coupled to the body 510 to form the female coupling device 500. Specifically, the bottom portion 514 includes post members 516 that engage the main body 510. The bottom portion 514 can be coupled to the main body 510 using various techniques, including staking and/or welding.

Such a configuration can be advantageous because the main body 510 (including the termination) can be molded as a single integral unit without any weld/joining lines. This results in a generally enclosed main body with a "solid shape" and relatively fewer components than a main body formed of multiple components. The bottom portion 514 can thereupon be coupled to the main body 510 as noted.

The female coupling device 500 also includes the seal 272 (see FIGS. 10-12 and 17-18) that is positioned within the main body 510 to seal against the mating male coupling device 300. This seal is similar or identical to that of the female coupling device 200 described above.

The seal 272 is held in place, at least in part, by the retaining member 274. The retaining member 274 is similar or identical to that of the female coupling device 200 describe above. As shown, for example, in FIGS. 17 and 37, after the seal 272 is placed within the body 510, the retaining member 274 is positioned within a front opening 517 of the main body 510. A groove 532 formed by the retaining member 274 engages a protrusion 518 formed by the front opening 517 of the main body 510 to hold the retaining member 274 in place. The retaining member 274 abuts the seal 272 and blocks the seal 272 from moving within the main body 510.

The retaining member 274 also includes openings 536 formed on opposing sides of the retaining member 274. These openings 536 provide clearance for the arms 258 when the clip member 250 is moved in the direction 254 to disengage the arms 258 from the clip groove 308 formed in the body 304 of the male coupling device 300. The arms 258 pass through the openings 536.

The retaining member 274 forms an opening 534 through which the mating male coupling device 300 extends when mated with the female coupling device 500. The bottom portion 514 also forms supporting structures 522, 524, 526 that help to support the retaining member 274 in position within the female coupling device 500.

Specifically, the supporting structures 522, 524, 526 help to hold a bottom surface 536 of the retaining member 274 and resist movement of the retaining member 274 and the mating male coupling device 300 that is inserted therethrough. This can be advantageous when, for example, forces are applied to the male coupling device 300. If, for example, an upward force (e.g., in a direction opposite the direction 254) is applied to the termination 302 of the male coupling device 300, the force would tend to cause the mating portion of the male coupling device 300 that is positioned in the retaining member 274 to move in the downward direction (i.e., the direction 254). The support structures 522, 524, 526 support the bottom surface 536 of the retaining member 274 to resist such forces to thereby retain the mating male coupling device 300 in position and coupled to the female coupling device 500.

In addition, the support structures 522, 524, 526 can function to strengthen the bottom portion 514 to enhance side load performance of the female coupling device 500. In this manner, loads that may be placed on the mating male coupling device 300 can be addressed with minimal impact to the performance of the female coupling device 500.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A female coupling device, comprising:
   a main body defining a fluid passage therethrough along a longitudinal axis of the female coupling device; and
   a clip member movably coupled to the main body, the clip member being movable transversely to the longitudinal axis between a locked position and an unlocked position, the clip member including two opposing cantilevered arms that extend at generally 45 degree angles relative to the longitudinal axis while the clip member is in the locked position,
   wherein transversely depressing the clip member relative to the main body moves: (i) the clip member toward the unlocked position, and (ii) the arms along a direction that is transverse to, and away from, the longitudinal axis.

2. The female coupling device of claim 1, wherein each of the arms includes an end that is contoured.

3. The female coupling device of claim 2, wherein the arms are configured to deform transversely outward away from the longitudinal axis.

4. The female coupling device of claim 1, further comprising at least one seal coupled to the main body and female coupling device, the seal being positionable to seal against a male coupling device when the male coupling device is inserted into the main body of the female coupling device.

5. The female coupling device of claim 4, further comprising a retaining member coupled to the main body and positioned to maintain the seal within the main body.

6. The female coupling device of claim 5, wherein the retaining member defines openings that the arms each pass through.

7. The female coupling device of claim 5, wherein the main body defines at least one support structure to engage the retaining member.

8. The female coupling device of claim 1, further comprising a termination configured to be coupled to a fluid line.

9. The female coupling device of claim 1, wherein the clip member is integrally molded the arms.

10. The female coupling device of claim 1, further comprising one or more springs that force the clip member toward the locked position.

11. The female coupling device of claim 10, wherein the one or more springs get compressed when the clip member is depressed relative to the main body.

12. A female coupling device, comprising:
a main body defining a fluid passage therethrough along a longitudinal axis of the female coupling device;
a clip member movably coupled to the main body, the clip member movable transversely to the longitudinal axis between a locked position and an unlocked position, the clip member including two opposing cantilevered arms that extend at acute angles relative to the longitudinal axis while the clip member is in the locked position; and
at least one seal coupled to the main body and positionable to seal against a male coupling device when the male coupling device is inserted the female coupling device; and
a retaining member coupled to the main body and positioned to maintain the seal within the female coupling device, wherein the retaining member defines openings that the arms each pass through,
wherein transversely depressing the clip member relative to the main body moves: (i) the clip member toward the unlocked position, and (ii) the arms along a direction that is transverse to, and away from, the longitudinal axis.

13. The female coupling device of claim 12, wherein the acute angle is generally 45 degrees.

14. The female coupling device of claim 12, wherein each of the arms includes an end that is contoured.

15. The female coupling device of claim 14, wherein the arms are configured to deform transversely outward away from the longitudinal axis.

16. The female coupling device of claim 12, wherein the clip member is integrally molded the arms.

17. The female coupling device of claim 12, further comprising one or more springs that force the clip member toward the locked position.

18. A coupling assembly, comprising:
a male coupling device defining clip groove; and
a female coupling device including:
  a main body defining a fluid passage therethrough along a longitudinal axis of the female coupling device;
  a clip member movably coupled to the main body, the clip member movable transversely to the longitudinal axis between a locked position and an unlocked position, the clip member including two opposing cantilevered arms that extend at acute angles relative to the longitudinal axis while the clip member is in the locked position;
  at least one seal coupled to the main body and positioned to seal against the male coupling device when the male coupling device is coupled with the female coupling device; and
  a retaining member coupled to the main body and positioned to maintain the seal within the female coupling device, wherein the retaining member defines openings that the arms each pass through,
wherein while the male coupling is coupled with the female coupling device and the clip member is in the locked position: (i) an end portion of each of the arms is positioned in the clip groove to lock the male coupling device to the female coupling device, and (ii) transversely depressing the clip member to the unlocked position causes the end portion of each of the arms to move out of the clip groove so that the male coupling is unlocked from, and free to be separated from, the female coupling device.

19. The coupling assembly of claim 18, wherein, as the male coupling device is inserted into the main body of the female coupling device, the arms deform transversely away from the longitudinal axis and contoured ends of the arms ride along an outer surface of the male coupling device before seating into the clip groove.

* * * * *

UNITED STATES PATENT AND TRADEMARK OFFICE
CERTIFICATE OF CORRECTION

PATENT NO. : 10,105,527 B2
APPLICATION NO. : 14/812085
DATED : October 23, 2018
INVENTOR(S) : Grant A. Wilhelm It is certified that error appears in the above-identified patent and that said Letters Patent is hereby corrected as shown below:

In the Claims

Column 6, Line 45-46: In Claim 4, after "and" delete "female coupling device, the seal being".

Column 7, Line 13: In Claim 12, after "inserted" insert -- into --.

Signed and Sealed this
Eighteenth Day of December, 2018

Andrei Iancu
*Director of the United States Patent and Trademark Office*